United States Patent [19]
Koller et al.

[11] Patent Number: 5,667,991
[45] Date of Patent: Sep. 16, 1997

[54] RECOMBINANT MERSACIDIN AND A METHOD FOR PRODUCTION

[75] Inventors: Klaus-Peter Koller, Bad Soden; Hans Georg Sahl; Gabriele Bierbaum, both of Bonn, all of Germany

[73] Assignee: Hoechst Aktiengesellschaft, Frankfurt am Main, Germany

[21] Appl. No.: 524,677

[22] Filed: Sep. 8, 1995

[30] Foreign Application Priority Data

Sep. 12, 1994 [EP] European Pat. Off. ............. 94114298

[51] Int. Cl.$^6$ .......................... C12P 21/06; C12N 1/20; A61K 38/00; C07H 19/00
[52] U.S. Cl. ................ 435/69.1; 435/252.3; 435/320.1; 514/9; 514/10; 530/317; 530/323; 536/22.1; 536/23.1; 536/23.7
[58] Field of Search .................... 435/69.1, 252.3, 435/320.1; 514/9, 10; 530/317, 323; 536/22.1, 23.1, 23.7

[56] References Cited

U.S. PATENT DOCUMENTS

5,112,806  5/1992  Chatterjee et al. ................ 514/9

OTHER PUBLICATIONS

Sahl, "Pore Formation in Bacterial Membranes by Cationic Lantibiotics", *Nisin and Novel Lantibiotics*, Proceedings of the First International Workshop on Lantibiotics, Apr. 15–18, 1991, ESCOM Leiden, pp. 347–358.

Southern, "Detection of Specific Sequences Among DNA Fragments Separated by Gel Electrophoresis, " *J. Mol. Biol.*, 98:503–517 (1975).

Chatterjee et al., "Mersacidin, A New Antibiotic From Bacillus Fermentation, Isolation, Purification and Chemical Characterization," *The Journal of Antibiotics*, 45(6):832–845 (1992).

Kupke et al., "Purification and Characterization of EpiD, a Flavoprotein Involved in the Biosynthesis of the Lantibiotic Epidermin, " *Journal of Bacteriology*, 174(16):5354–5361 (1992).

Somma et al., "Gardimycin, a New Antibiotic Inhibiting Peptidoglycan Synthesis, " *Antimicrobial Agents and Chemotherapy*, 11(3):396–401 (1977).

Marmur, "A Procedure for the Isolation of Deoxyribonucleic Acid from Micro–organisms, " *J. Mol. Biol.*, 3:208–218 (1961).

Birnboim et al., "A Rapid Alkaline Extraction Procedure for Screening Recombinant Plasmid DNA, " *Nucleic Acids Research*, 7(6) (1979).

Dente et al., "pEMBL: A New Family of Single Stranded Plasmids, " *Nucleic Acids Research*, 11(6) (1983).

Yanisch–Perron et al., "Improved M13 Phage Cloning Vectors and Host Strains: Nucleotide Sequences of the M13mp18 and pUC19 Vectors, " *Gene*, 33:103–119 (1985).

Augustin et al., "Genetic Analysis of Epidermin Biosynthetic Genes and Epidermin–Negative Mutants of *Staphylococcus epidermidis*, " *Eur. J. Biochem*, 204:1149–1154 (1992).

Weil et al., "Biosynthesis of the Lantibiotic Pep5: Isolation and Characterization of a Prepeptide Containing Dehydroamino Acids, " *Eur. J. Biochem*, 194:217–223 (1990).

Piard et al., "Structure, Organization, and Expression of 1ct Gene for Lacticin 481, A Novel Lantibiotic Produced by *Lactococcus lactis*, *The Journal of Biological Chemistry*, "268(22) :16316–16368 (1993).

Kaletta et al., "Pep5, A New Lantibiotic: Structural Gene Isolation and Prepeptide Sequence. " *Arch. Microbiol.*, 152:16–19 (1989).

Hynes et al., "Cloning of the Gene Encoding Streptococcin A–FF22, A Novel Lantibiotic Produced by *Streptococcus pyogenes*, and Determination of Its Nucleotide Sequence, " *Applied and Environmental Microbiology*, 59(6):1969–1971 (1993).

Jung, "Lantibiotics—Ribosomally Synthesized Biologically Active Polypeptides Containing Sulfide Bridges and $\alpha,\beta$–Didehydroamino Acids, " *Angewandte Chemie*, 30(9):1051–1192 (1991).

Bierbaum et al., "Lantibiotics—Unusually Modified Bacteriocin–like Peptides from Gram–Positive Bacteria, " *Zbl. Bakt.*, 278:1–22 (1993).

Beck–Sickinger et al., "Synthesis and Conformational Analysis of Lantibiotic Leader–, Pro–and Pre–peptides, " pp. 218–230.

Sanger et al., "DNA Sequencing With Chain–Terminating Inhibitors, " *Proc. Natl. Acad. Sci. USA*, 74(12):5463–5467 (1977).

*Primary Examiner*—Dian C. Jacobson
*Assistant Examiner*—Hyosuk Kim
*Attorney, Agent, or Firm*—Finnegan, Henderson, Farabow, Garrett & Dunner, L.L.P.

[57] ABSTRACT

The present invention refers in particular to the structural gene sequence of the peptide antibiotic mersacidin. Sequencing revealed that premersacidin consists of an unusually long 48 amino acid leader sequence and a 20 amino acid propeptide part (Seq. ID No:1) which is modified during biosynthesis to the mature lantibiotic.

13 Claims, 3 Drawing Sheets

```
        rbs                mrsA
CTTAATA AGGGGG TGAATACA ATG AGT CAA GAA GCT ATC ATT CGT TCA
                         M   S   Q   E   A   I   I   R   S TGG AAA GAT CCT TTT TCC CGT GAA AAT TCT ACA CAA AAT CCA GCT
 W   K   D   P   F   S   R   E   N   S   T   Q   N   P   A GGT AAC CCA TTC AGT GAG CTG AAA GAA GCA CAA ATG GAT AAG TTA
 G   N   P   F   S   E   L   K   E   A   Q   M   D   K   L GTA GGT GCG GGA GAC ATG GAA GCA GCA TGT ACT TTT ACA TTG CCT
 V   G   A   G   D   M   E   A   A   C   T   F   T   L   P
                                     ↑

GGT GGC GGC GGT GTT TGT ACT CTA ACT TCT GAA TGT ATT TGT TAA
 G   G   G   G   V   C   T   L   T   S   E   C   I   C   stop

TTTGATTTATATAGGCTGTTTCCCTTCAGAAGGAACAGCCTATATTTTATTATATAAACT
```

Fig. 3

Leader peptides

| Sequence | Name |
|---|---|
| MSTKDFNLDLVSVSKKDSGASPR | nisin |
| MSKFDDFDLDVVKVSKQDSKITPQ | subtilin |
| MEAVKEKNDLFNLDVVKESNDSGAEPR | epidermin |
| MKNNKNLFDLEIKKETSQNTDELEPQ | Pep5 |
| MKEQNSFNLLQEVTESELDLILGA | lacticin 481 |
| MEKNNEVINSIQEVSLEELDQIIGA | streptococcin A-FF 22 |
| MSQEAIIRSWKDPFSRENSTQNPAGNPFSELKEAQMDKLVGAGDMEAA | mersacidin |
| MTASILQQSVVDADFRAALLENPAAFGASAAALPTPVEAQDQASLDFWTKDIAATEAFA | cinnamycin |

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 68 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Met Ser Gln Glu Ala Ile Ile Arg Ser Trp Lys Asp Pro Phe Ser Arg
 1               5                  10                 15

Glu Asn Ser Thr Gln Asn Pro Ala Gly Asn Pro Phe Ser Glu Leu Lys
             20                  25                 30

Glu Ala Gln Met Asp Lys Leu Val Gly Ala Gly Asp Met Glu Ala Ala
         35                  40                 45

Cys Thr Phe Thr Leu Pro Gly Gly Gly Gly Val Cys Thr Leu Thr Ser
     50                  55                  60

Glu Cys Ile Cys
 65
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

```
Cys Thr Phe Thr Leu Pro Gly Gly Gly Gly Val Cys Thr Leu Thr Ser
 1               5                  10                 15

Glu Cys Ile Cys
             20
```

( 2 ) INFORMATION FOR SEQ ID NO:3:

( i ) SEQUENCE CHARACTERISTICS:
        ( A ) LENGTH: 201 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

```
ATGAGTCAAG AAGCTATCAT TCGTTCATGG AAAGATCCTT TTTCCCGTGA AAATTCTACA      60

CAAAATCCAG CTGGTAACCC ATTCAGTGAG CTGAAAGAAG CACAAATGGA TAAGTTAGTA     120

GGTGCGGGAG ACATGGAAGC ATGTACTTTT ACATTGCCTG GTGGCGGCGG TGTTTGTACT     180

CTAACTTCTG AATGTATTTG T                                               201
```

( 2 ) INFORMATION FOR SEQ ID NO:4:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

```
TGTACTTTTA CATTGCCTGG TGGCGGCGGT GTTTGTACTC TAACTTCTGA ATGTATTTGT        60
```

( 2 ) INFORMATION FOR SEQ ID NO:5:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Modified-site
        ( B ) LOCATION: one-of(2, 4, 13, 15)
        ( D ) OTHER INFORMATION: /note= "Xaa= aminobutryl residues."

( i x ) FEATURE:
        ( A ) NAME/KEY: Modified-site
        ( B ) LOCATION: one-of(16)
        ( D ) OTHER INFORMATION: /note= "Xaa= dehydrobutyrine."

( x i ) SEQUENCE DESCRIPTION: SEQ ID NO:5:

```
Ala  Xaa  Phe  Xaa  Leu  Pro  Gly  Gly  Gly  Gly  Val  Ala  Xaa  Leu  Xaa  Xaa
1                  5                        10                       15
Glu  Ala  Ile
```

( 2 ) INFORMATION FOR SEQ ID NO:6:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:6:

```
TTTACACTGC CTGGAGGAGG AGGAGTTTGT ACACTGACAT CAGAATGTAT C         51
```

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:7:

```
TCTCTTCCAT TTTTTTG         17
```

( 2 ) INFORMATION FOR SEQ ID NO:8:

( i ) SEQUENCE CHARACTERISTICS:
        ( A ) LENGTH: 19 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:8:

AAATCAAATT AACAAATAC                                                                 19

(2) INFORMATION FOR SEQ ID NO:9:

(i) SEQUENCE CHARACTERISTICS:
  (A) LENGTH: 48 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:9:

Met Ser Gln Glu Ala Ile Ile Arg Ser Trp Lys Asp Pro Phe Ser Arg
1               5                   10                  15

Glu Asn Ser Thr Gln Asn Pro Ala Gly Asn Pro Phe Ser Glu Leu Lys
            20                  25                  30

Glu Ala Gln Met Asp Lys Leu Val Gly Ala Gly Asp Met Glu Ala Ala
        35                  40                  45

(2) INFORMATION FOR SEQ ID NO:10:

(i) SEQUENCE CHARACTERISTICS:
  (A) LENGTH: 23 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:10:

Met Ser Thr Lys Asp Phe Asn Leu Asp Leu Val Ser Val Ser Lys Lys
1               5                   10                  15

Asp Ser Gly Ala Ser Pro Arg
            20

(2) INFORMATION FOR SEQ ID NO:11:

(i) SEQUENCE CHARACTERISTICS:
  (A) LENGTH: 24 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:11:

Met Ser Lys Phe Asp Asp Phe Asp Leu Asp Val Val Lys Val Ser Lys
1               5                   10                  15

Gln Asp Ser Lys Ile Thr Pro Gln
            20

(2) INFORMATION FOR SEQ ID NO:12:

(i) SEQUENCE CHARACTERISTICS:
  (A) LENGTH: 28 amino acids
  (B) TYPE: amino acid
  (C) STRANDEDNESS: single
  (D) TOPOLOGY: linear (ii) MOLECULE TYPE: peptide ( x i ) SEQUENCE DESCRIPTION: SEQ ID NO:12:

Met Glu Ala Val Lys Glu Lys Asn Asp Leu Phe Asn Leu Asp Val Lys
1               5                   10                  15

Val Lys Glu Ser Asn Asp Ser Gly Ala Glu Pro Arg
            20                  25

( 2 ) INFORMATION FOR SEQ ID NO:13:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:13:

Met Lys Asn Asn Lys Asn Leu Phe Asp Leu Glu Ile Lys Lys Glu Thr
1               5                   10                  15

Ser Gln Asn Thr Asp Glu Leu Glu Pro Gln
            20                  25

( 2 ) INFORMATION FOR SEQ ID NO:14:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:14:

Met Lys Glu Gln Asn Ser Phe Asn Leu Leu Gln Glu Val Thr Glu Ser
1               5                   10                  15

Glu Leu Asp Leu Ile Leu Gly Ala
            20

( 2 ) INFORMATION FOR SEQ ID NO:15:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:15:

Met Glu Lys Asn Asn Glu Val Ile Asn Ser Ile Gln Glu Val Ser Leu
1               5                   10                  15

Glu Glu Leu Asp Gln Ile Ile Gly Ala
            20                  25

( 2 ) INFORMATION FOR SEQ ID NO:16:

( i ) SEQUENCE CHARACTERISTICS:
        ( A ) LENGTH: 59 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:16:

Met Thr Ala Ser Ile Leu Gln Gln Ser Val Val Asp Ala Asp Phe Arg
1               5                   10                  15

| | | | | | | | | | | | | | | |
|---|---|---|---|---|---|---|---|---|---|---|---|---|---|---|
| Ala | Ala | Leu | Leu 20 | Glu | Asn | Pro | Ala | Ala 25 | Phe | Gly | Ala | Ser | Ala 30 | Ala | Ala |
| Leu | Pro | Thr 35 | Pro | Val | Glu | Ala | Gln 40 | Asp | Gln | Ala | Ser | Leu 45 | Asp | Phe | Trp |
| Thr | Lys 50 | Asp | Ile | Ala | Ala | Thr 55 | Glu | Ala | Phe | Ala | | | | | |

RECOMBINANT MERSACIDIN AND A METHOD FOR PRODUCTION

The present invention refers in particular to the structural gene sequence of the peptide antibiotic mersacidin. Sequencing revealed that premersacidin consists of an unusually long 48 amino acid leader sequence and a 20 amino acid propeptide part which is modified during biosynthesis to the mature lantibiotic.

Mersacidin belongs to a group of bactericidal peptides that was designated as lantibiotics in order to signify that these peptides contain the rare amino acids lanthionine and/or 3-methyllanthionine. Additional modified amino acids such as dehydroalanine and dehydrobutyrine occur regularly, while S-aminovinylcysteine and lysinoalanine are found in some lantibiotics only (G. Jung (1991), Angew. Chem. Int. Ed. Engl. 30: 1051–1068). Lantibiotics are produced by gram-positive bacteria and derived from ribosomally synthesized prepeptides. The lantibiotic structural genes have been found either on the bacterial chromosome (e.g. subtilin and cinnamycin, or are associated with movable elements like transposons (e.g. nisin) or large plasmids (e.g. epidermin and Pep5). The prepeptides consist of an N-terminal leader sequence that is cleaved off after export from the producer cell and the C-terminal propeptide, which is post-translationally modified to the mature lantibiotic (G. Jung (1991), supra). In a first step of the modification, serine and threonine residues are dehydrated to give dehydroalanine (Dha) or dehydrobutyrine (Dhb), respectively (H.-P. Well et al. (1990), Eur. J. Biochem. 194: 217–223). Subsequently the SH-groups of the cysteine residues react with the double bonds of Dha or Dhb residues to form the lanthionines or methyllanthionines, respectively.

Mersacidin was isolated from the culture supernatant of Bacillus spec. HIL Y-85,54728 and gained interest because of its significant in vivo efficiency against methicillin-resistant *Staphylococcus aureus* (MRSA) (S. Chatterjee et al. (1992), *J. Antibiotics* 45: 839–845). It is the smallest lantibiotic isolated so far (1825 Da), synthesized from a propeptide of 20 amino acids and contains 3 methyllanthionine residues, one dehydroalanine and one S-aminovinyl-2-methylcysteine (FIG. 1A) (S. Chatterjee (1992), *J. Antibiotics* 45: 832–838). Mersacidin carries no net charge and has overall hydrophobic properties. Recent results indicate that mersacidin interferes with the peptidoglycan biosynthesis. This occurs most likely on the level of transglycosylation via a mechanism which differs from antibiotics currently in use against MRSA.

Figure 2:
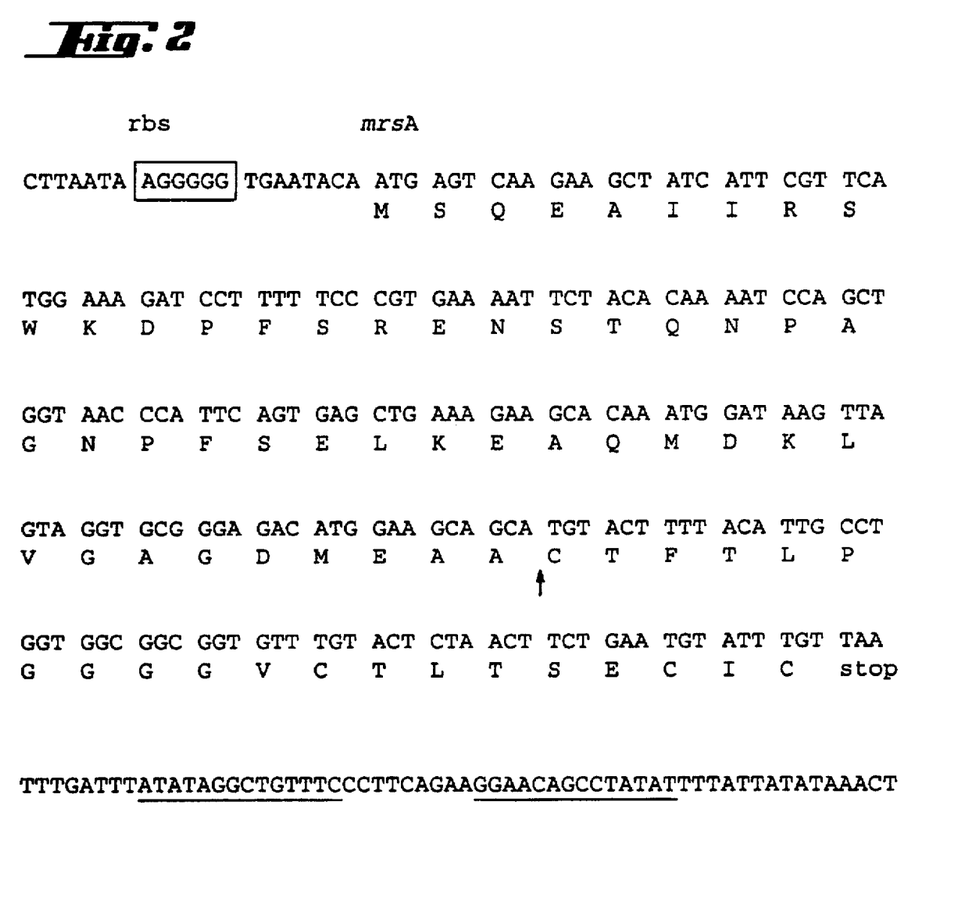
FIG. 2: Nucleotide sequence of the structural gene mrsA of the lantibiotic mersacidin (Seq. ID NO: 3) and deduced amino acid sequence of the prepeptide (Seq. ID NO: 4) The ribosome binding site in front of the ATG start codon is boxed and the processing site is marked by an arrow. The putative rho-independent terminator is underlined.

Therefore, the present invention refers to premersacidin having the amino acid sequence as shown in FIG. 2 from amino acid No. 1 through 68 (Seq. ID No:1) and promersacidin having the amino acid sequence as shown in FIG. 2 from amino acid No. 49 through 68. (Seq. ID No: 2)

A further embodiment of the present invention are DNAs coding for premersacidin or promersacidin, in particular DNAs having the nucleotide sequence as shown in FIG. 2 from No. 22 through 225 (Seq. ID No:3) encoding premersacidin or from No. 166 through 225 (Seq. ID NO:4) encoding promersacidin; a vector containing said DNA and a host cell containing said vector.

Another embodiment is a process for producing premersacidin, promersacidin or mature mersacidin by gene technological methods generally known by a skilled person in the art, i.e. a suitable host cell containing said DNAs coding for premersacidin or promersacidin are cultured under suitable conditions followed by isolation of premersacidin, promersacidin or mature mersacidin expressed by said host cell, preferably a gram-positive bacterium, such as Bacillus, Streptomyces or Streptococcus.

Finally, the premersacidin or promersacidin peptide or the genes thereof according to the present invention can be used for the production of mature mersacidin as, for example, described in WO 90/00558.

As an example, mature mersacidin is useful as peptide antibiotic for the preservation of foods particularly against methicillin-resistant *Staphylococcus aureus* or as an antibiotic to treat infections with *Staphylocoocus aureus* in animals or humans. The invention may further be used to obtain mersacidin derivatives modified in the amino acid sequence with an extruded antibiotic spectrum or a different efficacy. Furthermore, the invention opens ways to overexpress Mersacidin or its derivatives by genetic engineering.

DESCRIPTION OF THE FIGURES

FIG. 1: A) Structure of the lantibiotic mersacidin. (Seq. ID NO: 5) B) Putative prepeptide sequence and sequence of the 51 base guessmer that was used for identification of the structural gene. (Seq. ID NO: 6)

Conserved sequences have been marked in bold type. (Seq. ID NO: 10–16)

Example

1. Cloning of the structural gene of mersacidin

Figure 1:
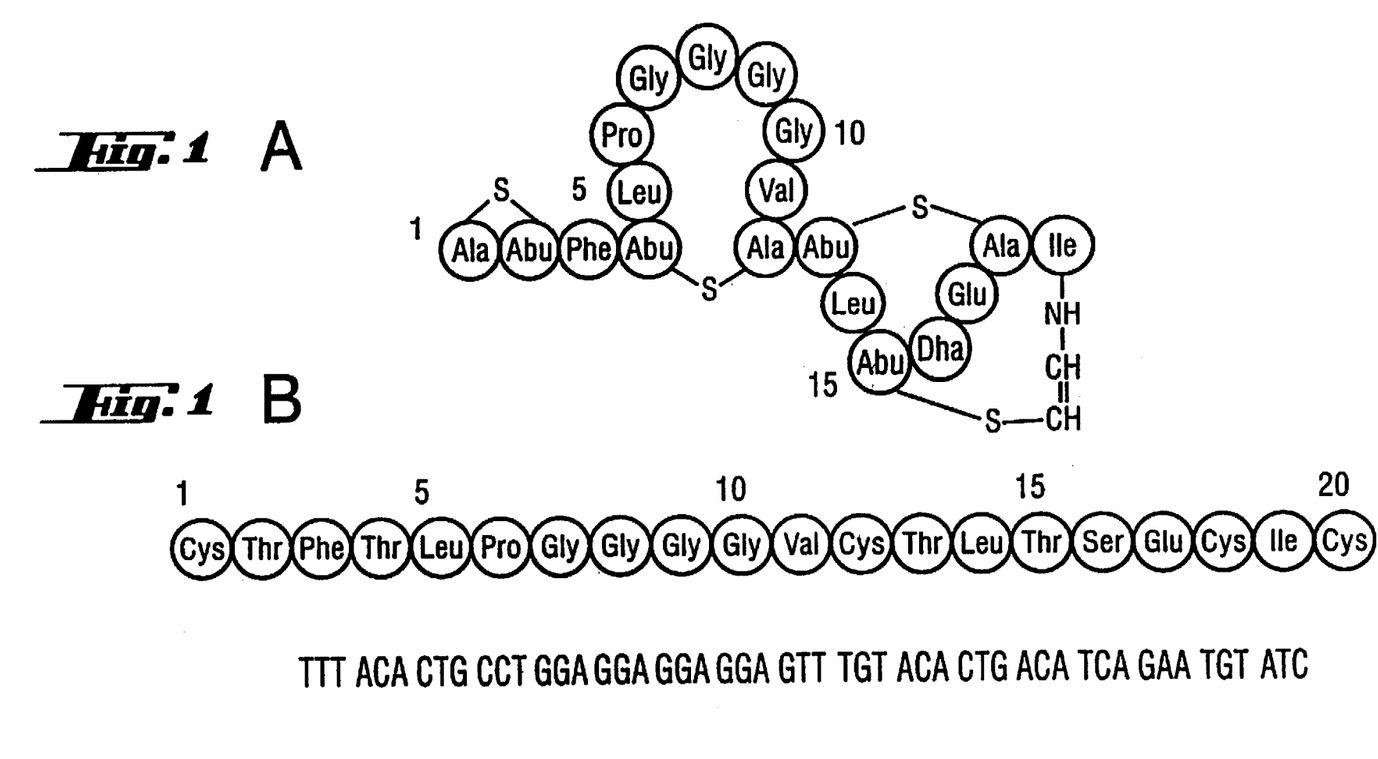

The putative mersacidin propeptide sequence (Seq. ID NO:6) (FIG. 1B) was deduced from the structure of mersacidin and based on general information about lantibiotic biosynthesis. The depicted probe was synthesized as a 51-base guessmer (Seq. ID NO: 6) based on preferred Codon usage of Bacillus on a PCR-Mate® (Applied Biosystems, Weiterstadt, FRG) and labeled with digoxigenin (Boehringer Mannheim, Mannheim, FRG) (FIG. 1B). The aminobutyryl residues (Abu$_s$-half of methyllanthionine) derive from threonines while the alanine residues (Ala$_s$-half of methylanthionine) are coded as cysteine in the propeptide. The-S-aminoviny-2-methylcysteine, that forms the terminal ring structure is probably formed from a methyllanthionine that has been oxidatively decarboxylated, as was shown for epidermin, which contains a C-terminal S-aminovinylcysteine (T. Kupke et al. (1992), *J. Bacteriol.* 174:5354–5361).

As plasmids could not be detected in the producer strain, chromosomal DNA was prepared as described by Marmur (J. Marmur (1961), *J. Mol. Biol.* 3: 208–218) except that only one chloroform extraction and precipitation were performed and that the DNA was subsequently dissolved in equilibration buffer and purified on a Qiagen-tip® 100 column (Diagen, Hilden, FRG). At 51° C. a single 2 kb band of a chromosomal restriction digest with Hind III hybridized with the probe in a Southern blot (E. M. Southern (1975), *J. Mol. Biol* 98: 503-517). The fragments ranging from 1.9 to 2.3 kb in size were cut out from the gel, eluted with a BIOTRAP® (Schleicher and Schüll Dassel, FRG) and subcloned in pUC18 (C. Yanisch-Perron et al. (1985), Gene 33: 103-109) in *E. coli*. The plasmids of several recombinant colonies were prepared by the Birnboim and Doly method (H. C. Birnbom and J. Doly (1979), Nucl. Acids Res. 7: 1513-1523), digested with Hind III and probed with the guessmer. One of the clones that gave a positive signal was further analyzed by restriction digests with various enzymes and subsequent Southern blots. Finally, a 1.3 kb EcoR I - Hind III fragment was subcloned into pEMBL 18 and pEMBL 19 (U Dente et al. (1983), Nucleic Acids. Res. 11: 1645-1655) in *E. coli*. Furthermore, a 0.6 kb EcoR V fragment was cloned in the vector pCU1 (J. Augustin et al. (1992), *Eur. J. Biochem.* 204:1149-1154) after site directed mutagenesis of the EcoR I site into an EcoR V site using the transformer site directed mutagenesis kit (Clontech, Palo Alto, USA).

2. Nucleotide sequence of the mersacidin structural gene, mrsA

The 0.6 kb fragment was sequenced on an A.L.F. automatic DNA sequencer (Pharmacia, Brussels, Belgium) using the dideoxy chain termination method (F. Sanger et ah (1977), *Proc. Natl. Acad. Sci. USA* 74: 5463-5467) from double stranded DNA; for priming the universal and reversal primer of the AutoRead® sequencing kit (Pharmacia, Brussels, Belgium) and two synthetic oligonucleotides 5'-TCTCTTCCATTTTTTTG)3' (Seq. ID NO: 7) and 5'-(AAATCAAATTAACAAATAC)3' (Seq. ID NO: 8) were employed. The nucleotide sequence of the mersacidin structural gene, mrsA, (Seq. ID NO: 3) is shown in FIG. 2. A potential ribosome binding site (AGG GGG) was found eight base pairs upstream of the ATG start codon of the open reading frame. The C-terminal part of the sequence is in agreement with the published mersacidin primary structure (S. Chatterjee et al. (1992), *J. Antibiotics* 45: 832-838) and its proposed propeptide sequence. The N-terminal part consists of a 48 amino acid leader sequence (Seq. ID NO: 9) (arrow in FIG. 2). The pro-mersacidin consists of 20 amino acids. Therefore, the full length of the prepeptide is 68 amino acids (Seq. ID NO: 1) with a calculated molecular mass of 7228 Da. Eight bases downstream of the TAA (ochre) stop codon, a hairpin structure with a free energy value of $-86.7$ kJ mol$^{-1}$ and a stem size of 14 base pairs was found, which could serve as a rho-independent terminator during transcription, as it is followed by a TTTATT sequence (FIG. 2).

3. Characterization of the mersacidin prepeptide

Lantibiotics have been subdivided into two groups (G. Jung (1991), supra). Type A-lantibiotics are elongated amphiphilic peptides that form transient pores in the membranes of sensitive bacteria (H.-G. Sahl (1991), Pore formation in bacterial membranes by cationic lantibiotics, p. 347-358. In G. Jung and H.-G. Sahl (ed.), Nisin and novel lantibiotics, Escom, Leiden). Type B-lantibiotics are globular peptides that are produced by Streptomyces, have molecular masses smaller than 2100 Da, and are highly homologous as to their amino acid sequence and ring structure, which includes a head to tail condensation (G. Jung (1991), supra). Up until now, mersacidin could not be classed with either group (G. Bierbaum and H.-G. Sahl (1993), Zbl. Bakt. 278: 1-22). In this respect, the comparison of the prepeptide sequence of mersacidin with that of type A- and B-lantibiotics is of special interest.

Figure 3:
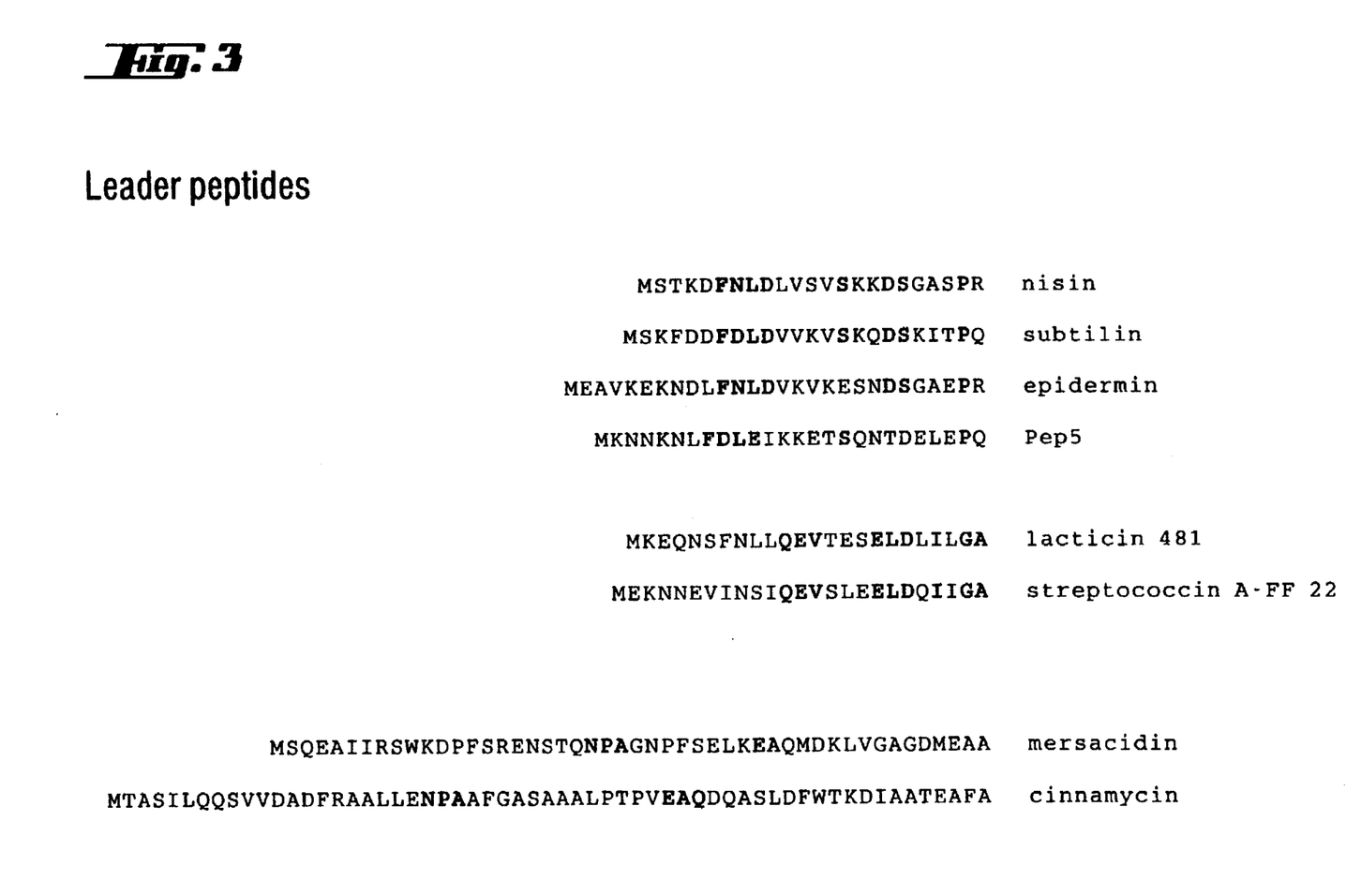
FIG. 3: Comparison of the leader sequences of several lantibiotics.

Two common characteristics of lantibiotic leader sequences have been preserved in mersacidin: i) There is no cysteine in the leader sequence (G. Jung (1991), supra), ii) An α-helix propensity is predicted for the C-terminal part of the leader sequence. Such structural elements have also been predicted and demonstrated for the leader peptides of type A-lantibiotis by circular dichroism measurements in trifluoroethanol/water mixtures (A. G. Beck-Sickinger and G. Jung. Synthesis and conformational analysis of lantibiotic leader-, pro- and prepeptides, p. 218-230. In G. Jung and H.-G. Sahl (ed.), Nisin and novel lantibiotics, Escom, Leiden 1991). In every other respect, the mersacidin leader sequence differs from the type A-lantibiotic leader sequences described so far. As shown in FIG. 3, it rather resembles in length and charge distribution (48 amino acids/ 12 charges) the unusually long 59 amino acid leader (11 charges) of the type B-lantibiotic cinnamycin (C. Kaletta et al. (1989), PepS, a new lantibiotic: structural gene isolation and prepeptide sequence. *Arch. Microbiol.* 152:16-19). In contrast, a typical highly charged type A-lantibiotic leader sequence, e.g. the Pep5 leader peptide, contains 10 charged residues in a total of only 26 amino acids (C. Kaletta et al. (1989), supra). Conserved sequences of type A-lantibiotics (e.g. the F D/N L D/E motif) are not found in the mersacidin leader peptide. The protease cleavage site of the mersacidin leader sequence ($^{-4}$M - $^{-3}$E - $^{-2}$A - $^{-1}$A - $^{+1}$C) differs from the conserved site of the type A-lantibiotics (FIG. 3). Here we find either the nisin type cleavage site (-1, positively charged amino acid; -2, proline; -3, negatively charged or polar and -4 hydrophobic) or the hydrophobic glycine containing cleavage sites of lacticin 481 J.-C. Piard et al. (1993), J. Biol. Chem., 268, 16361-16368 or streptococcin A-FF22 (W. U Hynes et al. (1993), *Appl. Env. Microbiol.* 59: 1969-1971). The ($^{-3}$A - $^{-2}$F - $^{-1}$A) cleavage site of cinnamycin (C. Kaletta et al. (1989), supra) conforms with the ($^{-3}$A - $^{-2}$X - $^{-1}$A) rule for proteins secreted via the Sec pathway. In conclusion, the mersacidin prepeptide shows no homologies to the conserved sequences of type A-lantibiotic leader sequences. There is similarity to the prepeptide of cinnamycin in length and charge distribution, but no obvious sequence homology on the amino acid level. Mersacidin is smaller than type A-lantibiotics, it is not positively charged, and it does not depolarize membranes, but rather inhibits peptidoglycan biosynthesis. This, in addition to the properties of the leader peptide indicates that mersacidin is more related to type B- than to type A-lantibiotics. Recently, the sequence and bridging pattern of another lantibiotic, actagardine, which also inhibits cell wall biosynthesis (S. Somma et al., *Antimicrob. Agents Chemother.* 11: 396-401, 1977), have been elucidated. Comparison to mersacidin shows that one ring is almost completely conserved in both lantibiotics. In view of the strong homology of the hitherto characterized type B-lantibiotics duramycin A, B, C, ancovenin and cinnamycin, these peptides could also be regarded as strutural variants as is observed for epidermin and gallidermin or nisin A and nisin Z. Therefore, we propose that mersacidin and actagardine should be classed with the type B-lantibiotics and that the designation type B-lantibiotic should not be exclusively reserved for strutureal variants of duramycin but comprise small, globular lantibiotics that carry a low charge and inhibit enzyme activity.

We claim:

1. A DNA coding for premersacidin having the amino acid sequence in FIG. 2 from amino acid No. 1 through 68 (SEQ ID NO: 1).

2. A DNA coding for premersacidin with the nucleic acid sequence as shown in FIG. 2 from nucleic acid No. 22 through 225 (Seq. ID No: 3).

3. A DNA coding for promersacidin having the amino acid sequence in FIG. 2 from amino acid No. 49 through 68 (SEQ ID NO:2).

4. A DNA coding for promersacidin having the nucleic acid sequence as shown in FIG. 2 from nucleic acid No. 166 through 225 (Seq. ID No: 4).

5. A vector containing a DNA as claimed in claim 1.

6. A host cell containing a vector as claimed in claim 5.

7. A process for producing premersacidin, promersacidin or mature mersacidin comprising the steps of:
   (a) culturing a suitable host cell containing a DNA sequence encoding one of Seq. ID Nos. 1 through 4 under suitable conditions; and
   (b) isolating premersacidin, promersacidin or mature mersacidin.

8. A vector containing a DNA as claimed in claim 4.

9. A vector containing a DNA as claimed in claim 3.

10. A vector containing a DNA as claimed in claim 2.

11. A host cell containing a vector as claimed in claim 10.

12. A host cell containing a vector as claimed in claim 9.

13. A host cell containing a vector as claimed in claim 8.

* * * * *